United States Patent [19]

Lamb

[11] Patent Number: 5,515,867
[45] Date of Patent: May 14, 1996

[54] HEAD SUPPORT FOR SHOULDER SURGERY POSITIONER

[75] Inventor: Steven R. Lamb, Union City, Calif.

[73] Assignee: Orthopedic System Inc., Union City, Calif.

[21] Appl. No.: 520,961

[22] Filed: May 30, 1995

[51] Int. Cl.⁶ .......................... A61G 15/00; A61B 19/00
[52] U.S. Cl. .................. 128/845; 128/869; 128/876
[58] Field of Search ....................... 128/845, 846, 128/869, 870, 873, 875, 876; 5/630, 636

[56] References Cited

U.S. PATENT DOCUMENTS

| | | | |
|---|---|---|---|
| 4,182,322 | 1/1980 | Miller | 128/869 |
| 4,267,830 | 5/1981 | Vick | 128/870 |
| 4,297,994 | 11/1981 | Bashaw | 128/869 |
| 5,014,374 | 5/1991 | Williams | 128/870 |
| 5,048,134 | 9/1991 | Dennill | 128/870 |
| 5,048,541 | 9/1991 | Haneline | 128/876 |

OTHER PUBLICATIONS

Orthopedic Systems, Inc., OSI Schlein Shoulder Positioner SSP-1000, 1991 (brochure).

*Primary Examiner*—Michael A. Brown
*Attorney, Agent, or Firm*—Bielen, Peterson & Lampe

[57] ABSTRACT

A patient head support for a shoulder surgery positioner having a headrest and a forehead band. The support includes a pad which is extendable over the chin of the patient. The pad possesses a soft outer surface. A pair of straps, each including first and second ends are connected to the pad at the first end thereof. Each of the straps also engage the headrest at the second end to adjustably hold the pad to the chin of the patient. A fastener is employed, such as a hook and pile arrangement. Such provision entails the fastener to include a member which extends along the pad and which is fixed relative to the pad to relieve tension of the pad. Thus, the pair of straps form adjustable closed loops relative to the pad.

5 Claims, 1 Drawing Sheet

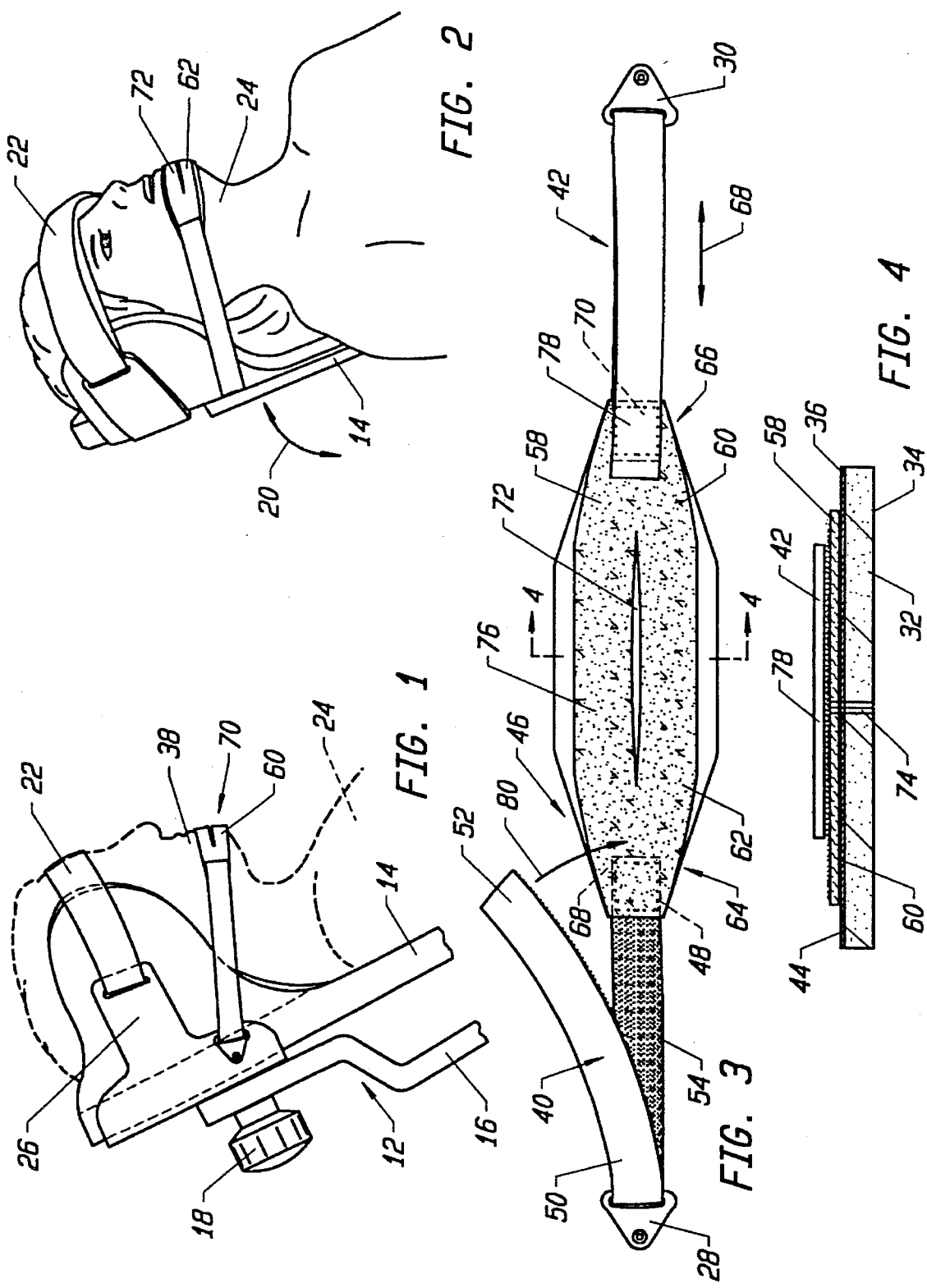

5,515,867

HEAD SUPPORT FOR SHOULDER SURGERY POSITIONER

BACKGROUND OF THE INVENTION

The present invention relates to a novel and useful patient head support for a shoulder surgery positioner.

A shoulder positioner is known in the medical arts to provide a support for seating a patient in a certain orientation for the purpose of arthroscopic and open shoulder surgery. For example, the O.S.I./Schlien shoulder positioner, model SSP-1000, available from Orthopedic Systems, Inc. of Union City, Calif., embodies such a shoulder surgery positioner. In essence, the patient is strapped into the positioner much the same as a person would sit in a beach chair. The waist portion and forehead of the patient is also strapped to prevent movement from the positioner. Recent modifications to shoulder positioners now permits the head and upper torso portion of the positioner to be rotated downwardly left or right to permit better access for the surgeon in such surgery. Extraneous motion of the head due to such tilting has been compensated by taping the head of the patient to the head support of the positioner.

Unfortunately, the taping of the head creates a problem of extreme discomfort and could put the patient at risk should cardiac arrest occur during the surgical procedure. In addition, the skin of the patient may be damaged during surgery through such taping procedure. Moreover, the lateral flexion adjustment of the surgery positioner is deactivated to a certain extent.

A head support for a shoulder surgery positioner which obviates the problems of the prior art system would be a notable advance in the medical field.

SUMMARY OF THE INVENTION

The present invention provides for a patient head support which is usable with a conventional shoulder surgery positioner.

The patient head support of the present invention utilizes a pad which extends over the chin of the patient. The pad is formed of soft material which has a soft outer surface that is intended for contacting the skin of the user without damage to the skin. For example, the pad may be formed of a delicate soft foam plastic material such as polyurethane, polypropylene, and the like. A pair of straps, each having first and second end portions, are utilized in conjunction with the pad. The first end portion of each strap is connected to the pad, directly or indirectly, and engages the headrest of the shoulder positioner intermediate the first and second portions. In other words, the pair of straps connected to the pad loop through the shoulder surgery positioner head support by the use of a rung, eye, or the like, provided by that device.

Fastening means is also included in the present invention for adjustably holding the second end portion of each of the pair of straps relative to the pad. Fastening means may include a first fastener portion attached to the second end portion of each strap. In addition, a second fastener portion is connected to the pad and extends along the pad. Such connection of the second fastener portion to the pad may take place in two places forming a central section of the second fastener portion which extends freely relative to the pad. Of course, each of the first fastener portions attached to the second end portions of each strap are capable of interlocking with the second fastening portion to form a closed loop relative to the headrest. In addition, the second fastener portion central section is sized to relieve tension force along the pad when the fastening means is tightened. Such a structure permits the use of a relatively soft and delicate pad in conjunction with a relatively strong fastening means. In certain cases, the fastening means may take the form of a hook and pile fastener system.

Further, the pad and the second fastener portion extending freely along side the pad includes a slit intended for accommodating at least a portion of the chin of the patient. Thus, the pad and associated second fastener portion do not slip relative to the chin of the patient, which avoids abrasion of the skin on the chin area of the patient.

It may be apparent that a novel and useful support for the head of a patient lying in a shoulder surgery positioner has been hereinabove described.

It is therefore an object of the present invention to provide a patient head support for a shoulder surgery positioner which further stabilizes the head of the patient by immobilizing the chin of the head, thus permitting the shoulder surgery positioner to tilt from a vertical axis.

Another object of the present invention is to provide a patient head support for a shoulder surgery positioner which avoids skin damage to the patient and is easily adjustable to accommodate patients of different sizes and configurations.

Another object of the present invention is to provide a patient head support for a shoulder surgery positioner which utilizes a relative soft chin pad and includes fastening means that may be tensioned without substantially tensioning the pad lying on the chin of the patient.

Yet another object of the present invention is to provide a patient head support for a shoulder surgery positioner which is easily attachable to a conventional shoulder surgery positioner and may be manufactured to be disposable after use.

Yet another object of the present invention is to provide a patient head support which is easily and quickly removable so the patient is not over-constrained in the event of inter operative cardiac arrest.

The invention possesses other objects and advantages especially as concerns particular characteristics and features which will become apparent as the specification continues.

BRIEF DESCRIPTION OF THE DRAWINGS

FIG. 1 is a side elevational view of the device of the present invention in place on a shoulder surgery positioner.

FIG. 2 is a left, front, isometric view of the head support of the present invention in place on a patient lying in a shoulder surgery positioner.

FIG. 3 is top plan view of the support of the present invention.

FIG. 4 is a sectional view taken along line 4—4 of FIG. 3.

For a better understanding of the invention reference is made to the following detail description of the preferred embodiments thereof which should be taken in conjunction with the hereinabove described drawings.

DETAILED DESCRIPTION OF THE PREFERRED EMBODIMENTS

Various aspects of the present invention will evolve from the following detailed description of the preferred embodiments thereof which should be referenced to the prior described drawings.

The invention as a whole is shown in the drawings by reference character 10. Patient head support 10 is employed in conjunction with a shoulder surgery positioner 12 which is known in the art. With reference to FIG. 1, positioner 12 is shown partially to include a headrest 14 and a support bracket 16. Knob 18 permits headrest 14 to rotate left or right according to directional arrow 20. In addition, positioner 12 is provided with a forehead band 22 which maintains the tension on the forehead of patient 24 by looping through flanges 26, one of which is shown on FIGS. 1 and 2. For example, positioner 12 may be a Schlien shoulder positioner, model SSP-1000 manufactured and distributed by Orthopedic Systems, Inc. of Union City, Calif.

Support 10 of the present invention utilizes rungs 28 and 30 which are connected to flange 26 and an identical flange on the other side of the patient 24, not shown. Rungs 28 and 30 may be held to positioner 12, by rivets, screws, welds, or any other known fastening means. Preferably, rungs 28 and 30 pivot relative to positioner 12. Support 10 further includes a pad 32 which is formed of any soft, pliable material such as a foam plastic. Pad 32 may be delicate to avoid damage to the skin of the user. Pad 32 includes a first side 34 and a second opposite side 36. First side 34 of pad 32 is intended to contact the chin area 38 of patient 24. It should be noted that pad 32 immobilizes the chin of the user when the positioner 12 is tilted.

Straps 40 and 42 are connected to pad 32 by any suitable means or formed integrally therewith. In the embodiment depicted in the drawings, straps 40 and 42 are sewn to the opposite extremities, 64 and 66, of pad 32. Straps 40 and 42 may be formed of cloth material, possessing flexibility. Soft layer of material 44 is attached or laminated to second side 36 of pad 32. Soft material layer 44 may be absorbent cotton, gauze, and the like.

Fastening means 46 is also depicted in the figures. Designating strap 44 as an exemplary strap, it may be observed that first end portion 48 is sewn to pad 32. Intermediate portion 50 passes through rung 28 while second end portion 52 extends back toward pad 32. Fastening means 46 may take many forms, however a hook and pile type fastener is shown in FIGS. 3 and 4. That is to say, strap 40 includes a surface 54 which provides the hook portion of the fastener. As heretofore noted, the same structure applies to strap 42. Thus, surface 54 may be deemed to be the first fastening portion 56 of fastening means 46. Second fastener portion 58 is also depicted in FIG. 3. Second fastener portion includes a strip 60 which extends along pad 32 second side 36. Surface 62 of second fastener portion strip 60 provides pile type material in the present embodiment. It should be noted that the attachment of strips 40 and 42 to pad 32 also includes sew lines 68 and 70 which hold strip 60 to ends 64 and 66 of pad 32. Most importantly, strip 60 is not attached between such fastening areas and is free to move relative to pad 32. Thus, any tensioning, directional arrow 68 by straps 40 and 42 would be taken up by strip 60 rather than pad 32. That is to say, strip 60 is sized to be equal to or less in length than pad 32 between the sew lines 68 and 70 holding straps 40 and 42, respectively to pad 32.

Slit 72 of strip 60 and slit 74 of pad 32, FIG. 4, generally align and permit at least a portion of the chin 38 to be accommodated thereby. Thus, pad and central portion 76 of strip 60 is stabilized around chin 38 of the user.

In operation, straps 40 and 42, connected to pad 32, are looped through rungs 28 and 30, respectively of headrest 14. Headrest 14 is part of a conventional shoulder surgery positioner 12 depicted in part in FIGS. 1 and 2. Second end portion 52 of strap 40 and end portion 78 of strap 42 are tensioned and placed atop surface 58 of strip 60 to complete the hook and pile fastening of the same. Directional arrow 80 depicts such exemplary movement with respect to strap 40. Pad 32 is not substantially tensioned since strap 60 takes up such tension force. Strip 60 also serves to back or support pad 32 outwardly from chin 38. Thus, the support 10 and pad 32 is firmly fastened on the chin 38 of the user patient 24. Slits 72 and 74 of strip 60 and pad 32, respectively, tend to open and accommodate or hold a portion of chin 38. Thus, support 10 does not slip relative to the chin 38 of patient 24 in this regard. With support 10 in place as shown in FIGS. 1 and 2 of the drawings, positioner 12 may be tilted left or right according to directional arrow 20 without movement of the patient's head. That is to say, the prior art forehead band 22 which was inadequate to prevent such head movement is supplemental by supported 10 to maintain the position of the head of patient 24 when headrest when headrest 14 is tilted, directional arrow 20.

While in the foregoing, embodiments of the present invention have been set forth in considerable detail for the purposes of making a complete disclosure of the invention, it may be apparent to those of skill in the art that numerous changes may be made in such details without departing from the spirit and principles of the invention.

What is claimed is:

1. A patient head support for a shoulder surgery positioner having a headrest and a forehead band comprising:
   a. a pad extendable over the chin of the patient, said pad possessing a soft outer surface;
   b. a pair of straps, each of said straps having a first and second end portion, said first end portion being connected to said pad, each of said straps adapted to engage the headrest intermediate said first and second end portion thereof;
   c. fastening means adjustably holding said second end portion of said pair of straps to said pad, said fastening means including first fastener portion attached to said second end portion of each strap and a second fastener portion connected to said pad and extending along said pad, each of said first fastener portions capable of interlocking with said second fastener portion to form a closed loop relative to the headrest, said second fastener portion including a central section adjacent to and free from said pad, said central section being sized to relieve tension force along said adjacent pad.

2. The support of claim 1 in which said fastening means is a hook and pile fastener.

3. The support of claim 1 in which said pad includes a first surface intended for contacting the patient, and a second opposite surface and further includes a soft absorbent layer fixed to said second opposite surface of said pads.

4. The support of claim 1 in which said pad and said second fastener portion each include a slit intended for accommodation at least a portion of the chin of the patient.

5. The support of claim 4 in which said second fastener portion connects to said pad on either side of said slits of said pad and said second fastener portion, said slit in said second fastener portion position in said central section thereof.

* * * * *